(12) United States Patent
Cordeiro Da Silva et al.

(10) Patent No.: US 8,350,036 B2
(45) Date of Patent: Jan. 8, 2013

(54) BISNAPHTHALIMIDOPROPYL DERIVATIVE COMPOUNDS WITH ANTI-PARASITE AND ANTI-CANCER ACTIVITY

(75) Inventors: Anabela Cordeiro Da Silva, Porto (PT); Joana Alexandra Pinto Da Costa Tavares, Oliveira De Azemeis (PT); Paul Kong Thoo Lin, Kingswells Aberdeen (GB)

(73) Assignee: Universidade Do Porto, Porto (PT)

( * ) Notice: Subject to any disclaimer, the term of this patent is extended or adjusted under 35 U.S.C. 154(b) by 791 days.

(21) Appl. No.: 12/159,755

(22) PCT Filed: Jun. 15, 2007

(86) PCT No.: PCT/IB2007/052311
§ 371 (c)(1),
(2), (4) Date: Jun. 30, 2008

(87) PCT Pub. No.: WO2008/007262
PCT Pub. Date: Jan. 17, 2008

(65) Prior Publication Data
US 2009/0062329 A1    Mar. 5, 2009

(30) Foreign Application Priority Data
Jun. 19, 2006  (FI) .......................... 103503

(51) Int. Cl.
*A61K 31/44* (2006.01)
*C07D 221/04* (2006.01)
(52) U.S. Cl. ......................... 546/98; 514/296
(58) Field of Classification Search .......... None
See application file for complete search history.

(56) References Cited

FOREIGN PATENT DOCUMENTS

| | | |
|---|---|---|
| DE | 42 32 739 A1 | 3/1994 |
| EP | 0 281 902 A1 | 9/1988 |
| WO | 91/18884 A1 | 12/1991 |
| WO | 95/29895 A1 | 11/1995 |

OTHER PUBLICATIONS

Tavares, J., et al., "Differential effects of polyamine derivative compounds against *Leishmania infantum* promastigotes and axenic amastigotes," International Journal of Parasitology, Pergamon Press, GB, May 1, 2005, vol. 35, No. 6, pp. 637-646.
Dance, A.M., et al., "Synthesis and biological activities of bisnaphthalimidopolyamines derivatives: cytotoxicity, DNA binding, DNA damage and drug localization in breast cancer MCF 7 cells," Biochemical Pharmacology, Pergamon, Oxford, GB, Jan. 1, 2005, vol. 69, No. 1, pp. 19-27.
Lin, P.K.T., et al., "The synthesis and in vitro cytotoxic studies of novelbis-naphthalimidopropyl polyamine derivatives," Bioorganic & Medicinal Chemistry Letters, Oxford, GB, Jul. 17, 2000, vol. 10, No. 14, pp. 1609-1612.
Lin, P.K.T., et al., "The biological activities of new polyamine derivatives as potential therapeutic agents," Biochemical Society Transactions, 2003, vol. 31, No. 2, pp. 407-410.
Tavares, J. et al., "Anti-leishmanial activity of the bisnaphthalimidopropyl derivatives," Parasitology International, vol. 61, pp. 360-363 (2012).
Tavares, J. et al., "Bisnaphthalimidopropyl Derivatives as Inhibitors of *Leishmania* SIR2 Related Protein 1," ChemMe Chem, vol. 5, pp. 140-147 (2010).

*Primary Examiner* — Janet Andres
*Assistant Examiner* — Heidi Reese
(74) *Attorney, Agent, or Firm* — Sughrue Mion, PLLC

(57) ABSTRACT

The present invention relates to chemical compounds with anti-cancer and anti-parasite activity. The invention relates, above all, to novel bisnaphthalimidopropyl derivatives with specific cytotoxic activity towards human cancer cells and protozoan cells capable of causing parasitic diseases in humans. The invention further relates to chemical compounds to be administered especially to humans and in particular for therapeutic use.

8 Claims, 1 Drawing Sheet

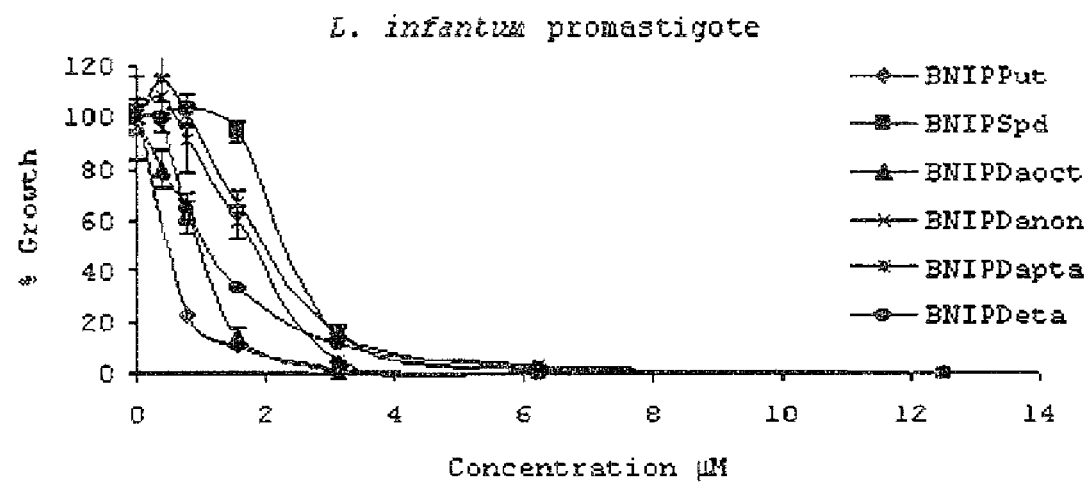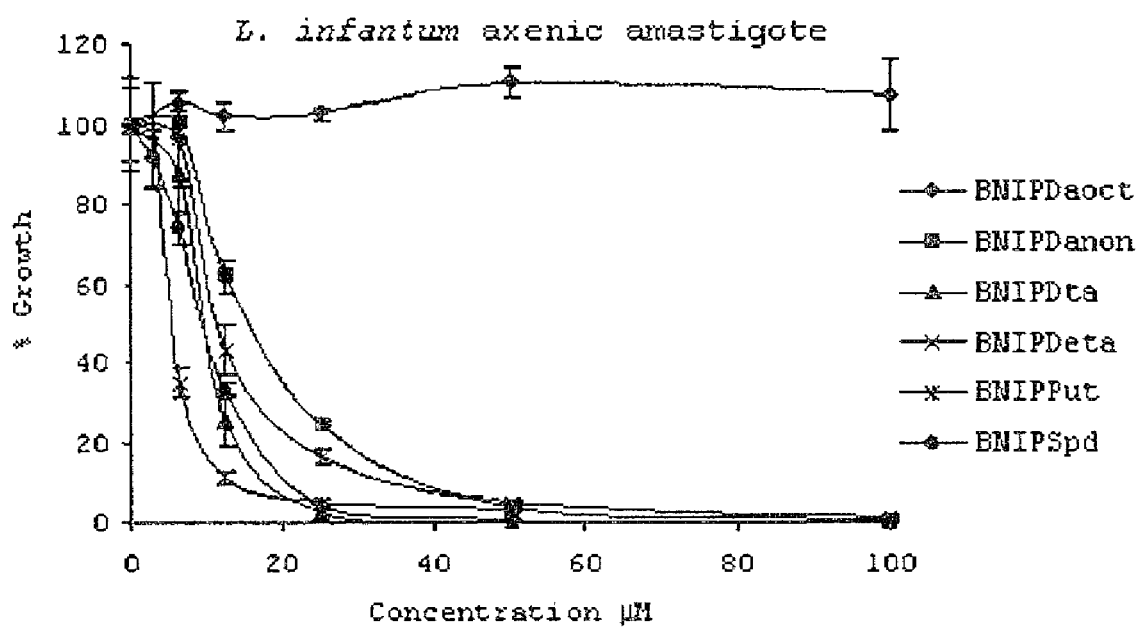

BISNAPHTHALIMIDOPROPYL DERIVATIVE COMPOUNDS WITH ANTI-PARASITE AND ANTI-CANCER ACTIVITY

TECHNICAL DOMAIN OF THE INVENTION

The new bisnaphthalimidopropil derivatives, preparation process thereof, pharmaceutical composition comprising them and their use in cancer and parasitic diseases, namely leishmaniasis, trypanosomiasis and malaria, with pharmaceutical industry application.

The present invention referred to a preparation process of the new bisnaphthalimidopropil derivative compounds and pharmaceutical compositions comprising them. These compounds have a role in the growth inhibition of the parasite protozoa *Leishmania infantum* and cytotoxic properties on cancer cells.

PREVIOUS STATE OF ART

Naphthalimido derivatives exhibit considerable potential as cytotoxic agents for cancer chemotherapy (Brana et al., 2001). We previously reported the synthesis and biological activities of a novel series of bisnaphthalimidopropyl polyamines compounds (Kong et al., 2000). Subsequent work revealed the presence of the bisnaphthalimidopropyl functionality to be essential for optimum biological activity since the presence of an oxygen atom in the α-position of the naphthailimido ring tends to reduce activity (Pavlov et al., 2001).

Majority research traditionally focused on the modification of the naphthalimido rings to enhance anticancer activities through increased DNA binding and cleavage. For example, acenaphthalimide was introduced into the naphthalimide chromophore to increase the solubility of the bisnaphthalimide compounds (Patten et al., 1992). Furan heterocycles were added to the naphthalimide chromophore and those compounds exhibited strong DNA binding properties with toxicity to CEM leukaemia cells to be in the nanomolar concentration (Brana et al., 1995). Pyrazine heterocycles have also recently been fused to naphthalimides and those pyrazino-naphthalimides exhibited in vitro toxicity with $IC_{50}$ values ranging from 0.002 to 7.8 μM after 72 hour treatment in cancer HT 29, HeLa, and PC 3 cells (Bailly et al., 2003).

However, in our laboratory we have developed bisnaphthalimidopropyl fragments linked to natural polyamines such as putrescine, spermidine and spermine. The spermidine and spermine derivatives exhibited enhanced aqueous solubility while maintaining good biological activity (Carrasco et al., 2003 and Kong et al., 2003). In MCF 7 breast cancer cells, compounds were observed within the cell nuclei after 6 and 12 hour drug exposure, with transport being potentially energy dependent (Dance et al., 2005). Within MCF7 cells, the bisnaphthalimidopropyl compounds inflicted significant quantitative DNA damage. We also found for the first time that bisnaphthalimido propyl derivatives exert significant anti-proliferative effects on the life cycle of *Leishmania infantum*, the causative agent of visceral leismaniasis and these drugs also induced the death of promastigotes by apoptosis (Tavares et al., 2005).

In the leishmaniasis the first line chemotherapy is restricted to the use of pentavalent antimony derivatives (Murry et al., 2001). As a consequence of the long course of the therapy, the adverse reactions appear and the resistances induce the search of new drug more efficient. The efficacy of the treatment be also comprised in immunodeficiency situation, namely in the co infection *Leismania*/HIV.

The natural polyamine, putresceine, spermidine, and spermine are present in most eukaryotic cells and have an important role on proliferation and cellular differentiation (Muller et al., 2001). In the case of trypanosomatids polyamines have an additional role in the endogenous oxi-redox equilibrium by the trypanothione compound [N1,N8-bis(glutathione)spermidine]. This molecule and the associated enzymatic reactions have been considered as good drug targets (Fairlamb and Cerami, 1992; Barrete et al., 1999). The search for compounds which interfere with the regulatory function of the polyamines represents a new strategy for finding new compounds with anti-cancer and anti-parasitic activity. Polyamine synthesis inhibitors such as α-DFMO (alpha-difluormethylornitine) have been shown to be active against different stages in the life cycle of the parasite *Plasmodium* sp. This parasite has a bifunctional enzyme with ornithine and S-adenosylmethionine decarboxilase activity, that hence became attractive as a drug target since it is absent in the host cells (Muller et al, 2001).

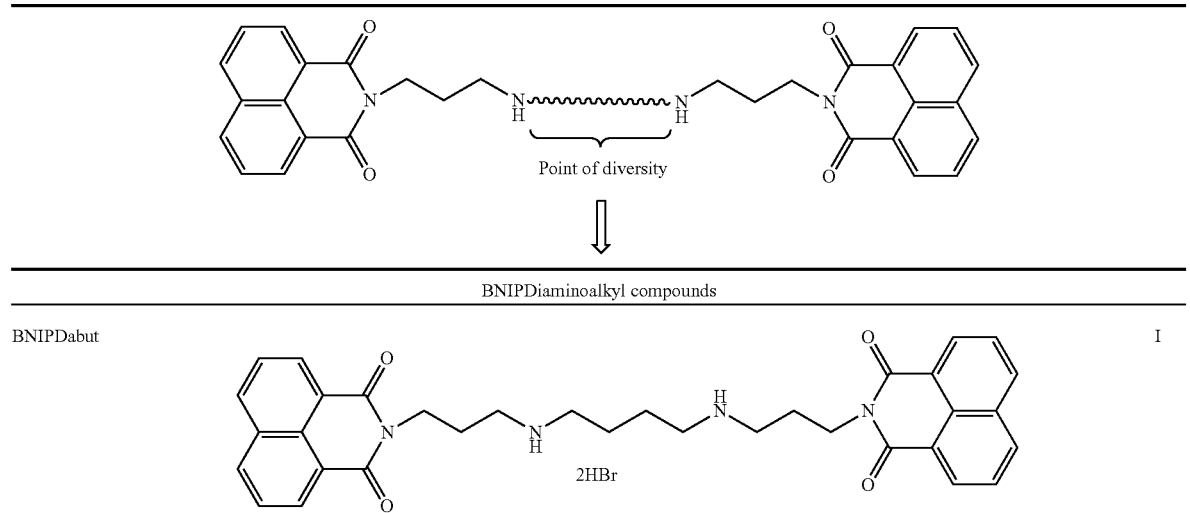

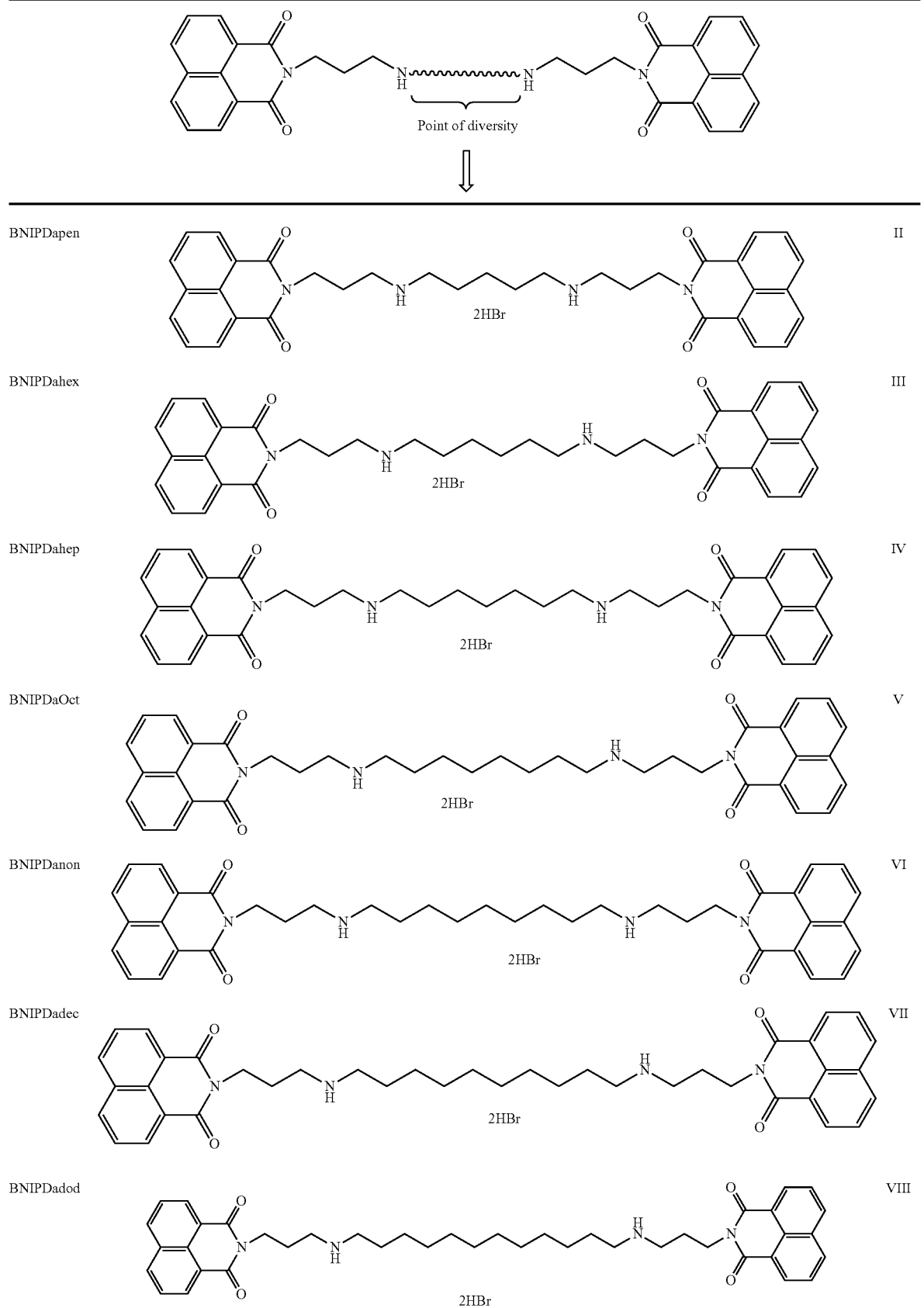

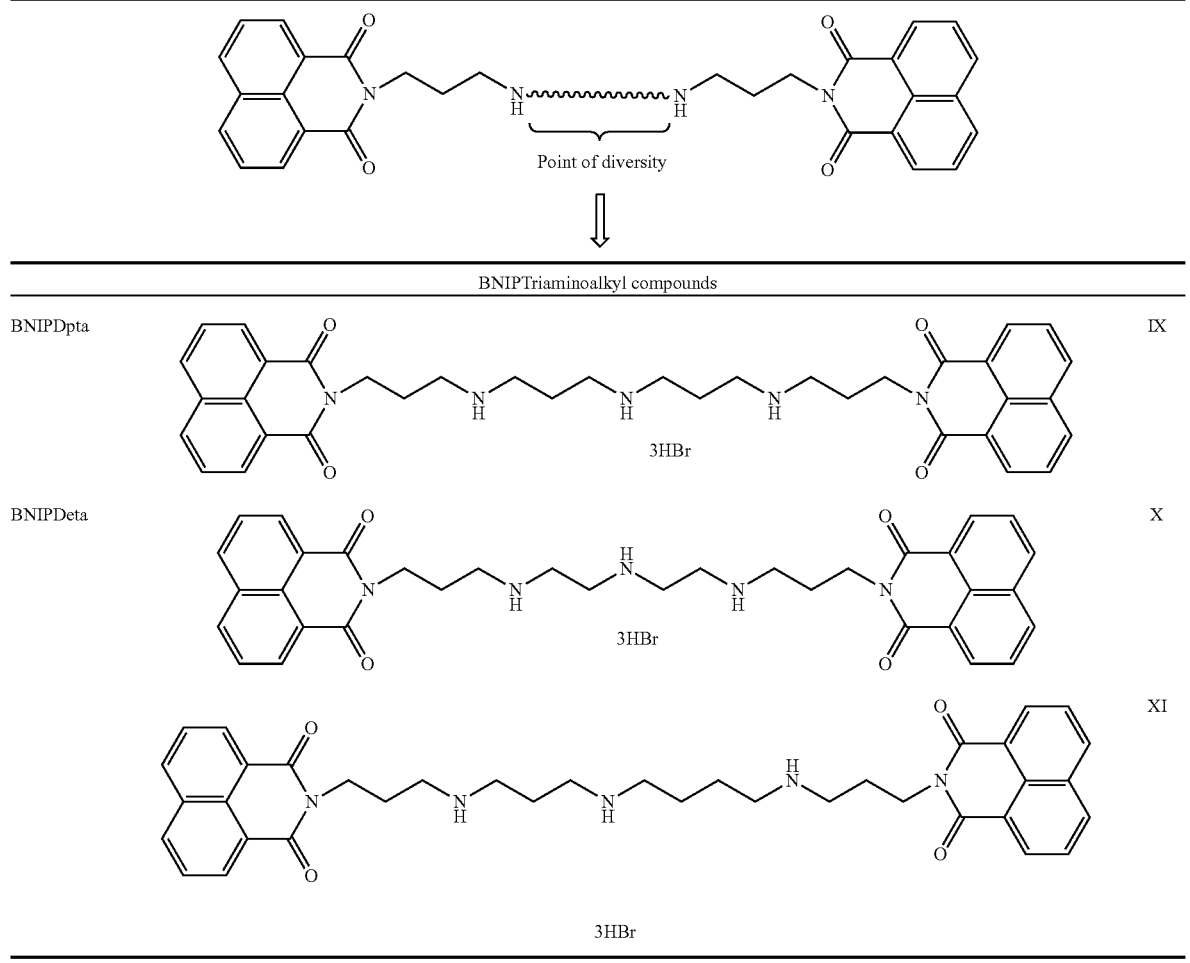

wherein:
the alkyl central chain has modifications in the length and in the introduction of nitrogen atoms.
The compounds showed in formulation A are:
1. Bisnaphthalimidopropylputrescine—BNIPPut (I)
2. Bisnaphthalimidopropyldiaminopentane—BNIPDapen (II)
3. Bisnaphthalimidopropyldiaminohexane—BNIPDahex (III)
4. Bisnaphthalimidopropyldiaminoheptane—BNIPDahep (IV)
5. Bisnaphthalimidopropyldiaminooctane—BNIPDaoct (V)
6. Bisnaphthalimidopropyldiaminononane—BNIPDanon (VI)
7. Bisnaphthalimidopropyldiaminodecane—BNIPDadec (VII)
8. Bisnaphthalimidopropyldiaminododecane—BNIPDadod (VIII)
9. Bisnaphthalimidopropyldipropiltriamine—BNIPDpta (IX)
10. Bisnaphthalimidopropyldietiltriamine—BNIPDeta (X)
11. Bisnaphthalimidopropylespermidine—BNIPSpd (XI)

Another aspect of the invention concern the preparation process, pharmaceutical formulation made in combination of one compound of formula II, III, IV, VI, VII, VIII, IX, X with a vehicle or safety pharmaceutical excipient.

DESCRIPTION OF THE INVENTION

The synthesis of the protected compounds in this invention was based on methods previously described by our group (Kong et al., 2003). The bisnaphthalimido compounds with linker chain containing 2 nitrogens were previously synthesised by simply reacting the corresponding alkyltetraamine with 1,8-naphthalic anhydride (Brana et al., 1995). In order to introduce more heteroatoms in the linker chain, N-alkylation reaction was chosen according to a Kong modified method (Kong et al., 1998). The common intermediate for the synthesis of different compounds was toluenesulfonyloxypropylnaphthalimide. This was prepared by first reacting 1,8-naphthalic anhydride with aminopropanol to give N-(3-hydroxypropyl)naphthalimide which upon reaction with tosyl chloride gave toluenesulfonyloxypropylnaphthalimide, with 60% yield. To obtain the bisnaphthimide the polyamine used depends on the compound to synthesise and were first protected with 2,4,5-trimethylsulphonyl chloride (Mts-Cl) in pyridine followed by their N-alkylation with toluenesulfonyloxypropylnaphthalimide produced the bisnaphthalimide derivative protected. The deprotection was obtained with hydrobromic acid/glacial acetic acid in dichloromethane to give the respective derivative as their hydrobromide salts.

CaCo-2 cells (ECACC, 86010202) were obtained from the European Collection of Cell Cultures. All reagents were purchased from Aldrich, Fluka and Lancaster and were used without purification. TLC was performed on Kieselgel plates (Merck) 60 $F_{254}$ in chloroform:methanol (97:3 or 99:1). Column Chromatography was done with silica gel 60, 230-400 meshes using chloroform and methanol as eluent. FAB-mass spectra were obtained on a VG Analytical AutoSpec (25 Kv) spectrometer; EC/CI spectra were performed on a Micromass Quatro II (low resolution) or a VG Analytical ZAB-E instrument (accurate mass). $^1$H and $^{13}$C NMR spectra were recorded on a JEOL JNM-EX90 FT NMR spectrometer.

BNIPSpd and BNIPPut were synthesised according to our methods previously reported (Kong et al, 2003 and Tavares et al., 2005).

Cytotoxicity Studies

Cytotoxity was evaluated for CaCo-2 colon carcinoma using the MTT assay with protocols appropriate for the individual test system.[11,13] CaCo-2 cells were maintained in Earle's Minimum Essential Medium (Sigma), supplemented with 10% fetal calf serum (Biosera), 2 mM L-glutamine (Sigma), 1% non-essential amino acids (Sigma), 100 IU mL$^{-1}$ penicillin and 100 μg mL$^{-1}$ streptomycin (Sigma). Exponentially growing cells were plated at $2\times10^4$ cells cm$^{-2}$ into 96-well plates and incubated for 24 h before the addition of drugs. Stock solutions of compounds were initially dissolved in 20% DMSO and further diluted with fresh complete medium. After 24 and 48 h of incubation at 37° C., the medium was removed and 200 μl of MTT reagent (1 mg/mL) in serum free medium was added to each well. The plates were incubated at 37° C. for 4 h. At the end of the incubation period, the medium was removed and pure DMSO (200 μl) was added to each well. The metabolized MTT product dissolved in DMSO was quantified by reading the absorbance at 560 nm on a micro plate reader (Dynex Technologies, USA). $IC_{50}$ values are defined, as the drug concentrations required to reduce the absorbance by 50% of the control values. The $IC_{50}$ values were calculated from the equation of the logarithmic line determined by fitting the best line (Microsoft Excel) to the curve formed from the data. The $IC_{50}$ value was obtained from the equation for y=50 (50% value).

*Leishmania infantum* (clone MHOM/MA671TMA-P263) promastigotes transfected with reporter gene that encode to the luciferase enzyme (Roy et al, 2000) were grown at 27° C. in RPMI medium (Gibco) supplemented with 10% of heat inactivated fetal bovine serum (FBS-Gibco), 2 mM L-glutamine (Gibco), 20 mM Hepes (Gibco), 100 U/ml penicillin (Gibco) and 100 μg/ml streptomycin (Gibco). The parasites ($10^6$/ml) in the logarithmic phase (2 days of culture) were incubated with a serial range of concentrations of each drug for 3 days at 27° C. and the growth of parasites was determined by using the luciferase activity using luciferin as subtract.

The axenic amastigote of *Leishmania infantum* (clone MHOM/MA671TMA-P263) transfected with reporter gene that encode to the luciferase enzyme (Roy et al, 2000) were grown at 37° C. with 5% $CO_2$ in a cell-free medium called MAA (medium for axenically grown amastigote). The medium MAA/20, consisted of modified medium 199 (Hanks' balanced salts) supplemented with 0.5% soya tryptocasein, 15 mM D-glucose, 5 mM L-glutamine, 4 mM $NaHCO_3$, 0.023 mM bovine hemin, 25 mM HEPES final pH, 6.5 and 20% inactivated fetal calf serum. The parasites were incubated with different concentrations during 3 days at 37° C. with 5% $CO_2$. The growth of the parasites was done by measuring the luciferase activity using luciferin as a substract. The intracellular amastigotes of *L. infantum* were cultured in a macrophage differentiated human leukemia monocyte cell line (THP-1 cells). The THP-1 cells were differentiated during 2 days with 20 ng/ml of PMA in RPMI-1640 medium supplemented with 10% FCS, 2 mM glutamine, 100 IU of penicillin/ml and 100 μg/ml of streptomycin. The non differentiated cells were washed with pre-warmed medium and the adherent cells sinfected with luciferase-expressing axenic amastigotes at a parasite/macrophage ratio of 3:1 for 4 h at 37° C. with 5% $CO_2$. Noninternalized parasites were removed and serial dilutions of each drug were made in the RPMI medium supplemented with 10% FCS. After 3 days of drug exposure, wells containing adherent differentiated THP-1 cells were washed and luciferase activity was determined.

Results

Chemistry

The synthetic strategy adopted to synthesise bisnaphthalimidopropyl derivatives BNIPDapen, BNIPDhex, BNIPDahep, BNIPDaoct, BNIPDanon, BNIPDadec, BNIPDadod, BNIPDpta, BNIPDeta based on methods previously developed in our laboratory (Kong et al, 2000). Protection and activation of all the di- and tri-amines were carried with mesitylene chloride in pyridine at room temperature to give compounds 1-5 in high yield. N-alkylation of the latter compounds with O-tosylpropylnaphthalimide 6 with Ceasium carbonate in anhydrous DMF, afforded the fully protected Bisnaphthalimidopropyl derivatives which upon deprotection with hydrobromic acid/glacial acetic acid in $CH_2Cl_2$ gave BNIPDapen, BNIPDhex, BNIPDahep, BNIPDaoct, BNIPDanon, BNIPDadec, BNIPDadod, BNIPDpta, BNIPDeta in yield varying from 50-70%.

Scheme 1. Synthetic strategy for the synthesis of Bisnaphthalimidopropylal-kylamines derivatives.

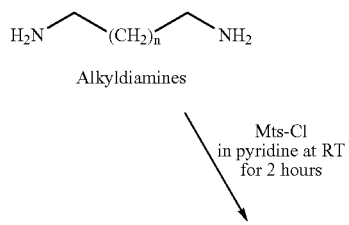

Alkyldiamines

Mts-Cl
in pyridine at RT
for 2 hours

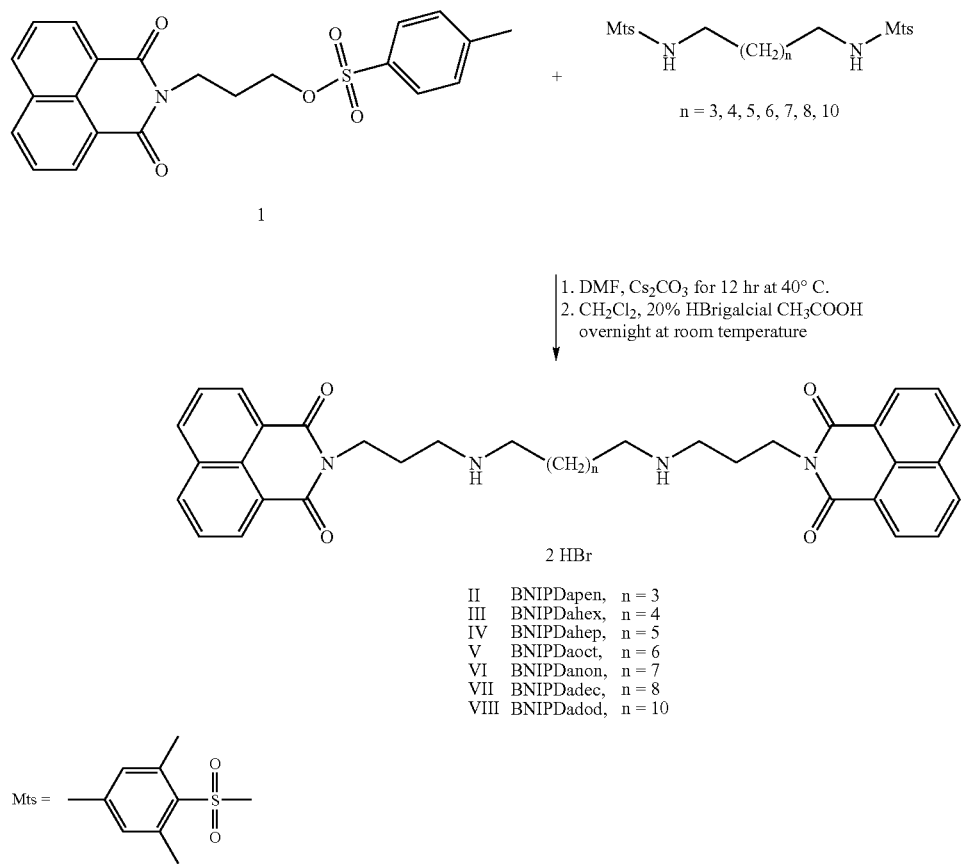
Scheme 2. Synthesis of Bisnaphthalimidopropylalkyltriamines.
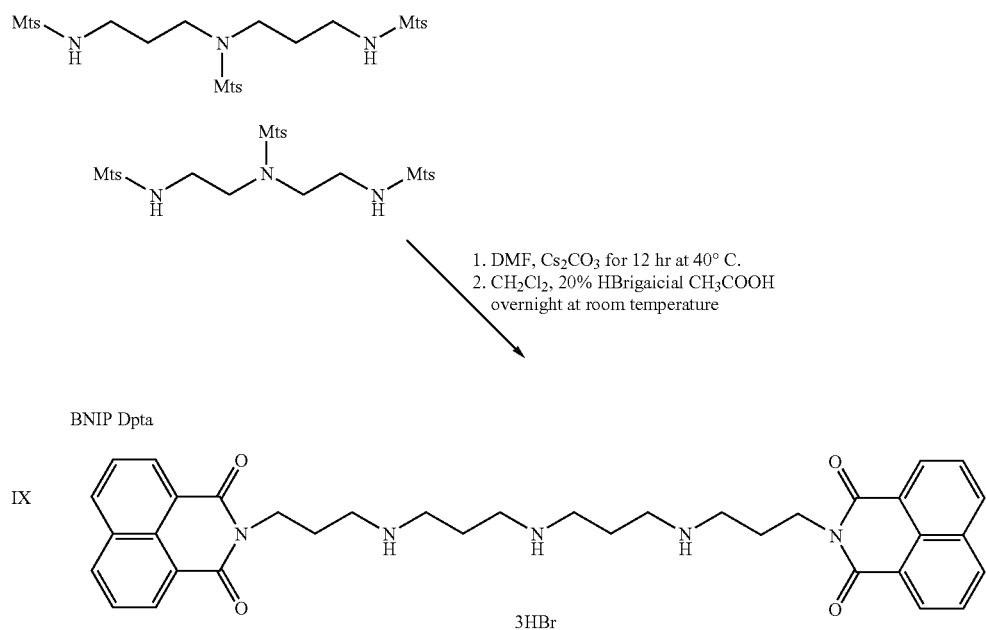

BNIP Deta

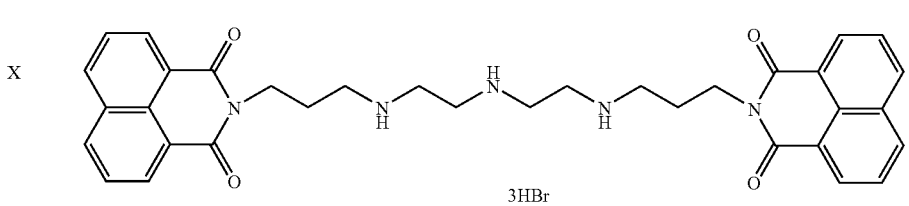

Biological Activities

The in vitro cytotoxicity of all the bisnaphthalmidopropyl derivatives described above were studied against colon cancer cell lines CaCo-2 and parasite *Leishmania infantum*. In the cancer cell line the $IC_{50}$ values of each compound were determined after 24 and 48 hr drug exposure (Table 1). All compounds except for BNIPDeta ($IC_{50}$ values, 21.7 and 22.3 µM for 24 and 48 h respectively exerted $IC_{50}$ values between 0.15 and 8.00 µM. BNIPSpd was the most active compound ($IC_{50}$, 0.15 and 0.47 µM at 24 and 48 h respectively). In the same order of activity, the compound BNIPDadec showed a $IC_{50}$ 0.77 and 0.36 µM, after 24 h and 48 h of incubation, respectively.

The removal of a nitrogen atom from the linker chain does not appear to substantially affect the cytotoxic properties of these compounds. We previously reported that when the central alkyl group is a butyl chain, the compound (BNIPPut) is not soluble in most solvents and the aqueous solubility of bisnapthalimidopropyl compounds is enhanced by introducing a heteroatom like nitrogen in the central chain (Kong et al, 2000). Here, by increasing the length of the alkyl central chain such as in BNIPDao, BNIPDan and BNIPDad, also helps aqueous solubility. We reason that with the longer alkyl chain, the two naphthalimido rings do not tend to stack on top of each other by $\pi$-$\pi$ interactions between the aromatic rings and hence favour aqueous solubility. Among the latter compounds, BNIPDad showed the highest cytotoxicity against Caco-2 cells with $IC_{50}$ values of 0.36 µM (48 hr) and 0.77 µM (24 hr).

TABLE 1

Cytotoxicity of polyamine analogues against CaCo-2 cancer cells

| Compound[a] | $IC_{50}$ (µM) | |
|---|---|---|
| | 24 h | 48 h |
| BNIPSpd | 0.15 | 0.47 |
| BNIPPut | ND | ND |
| BNIPDapen | 11.00 | 6.50 |
| BNIPDahex | 0.65 | 2.00 |
| BNIPDahep | 3.20 | 0.94 |
| BNIPDaoct | 6.20 | 3.20 |
| BNIPDanon | 3.60 | 0.67 |
| BNIPDadec | 0.77 | 0.36 |
| BNIPDadod | 4.50 | 2.70 |
| BNIPDpta | 5.00 | 3.20 |
| BMPDeta | 21.70 | 22.30 |

[a]Cytotoxicity determined by MTT assay. Data obtained after treating Caco-2 cells with varying concentrations of analogues (0.01-40 µM) for 24 and 48 hours. Data are mean ± SD of 6 replicates. ND: not determined.

FIG. 1. A dose-response growth curve of luciferase promastigote and axenic amastigote forms demonstrating the in vitro effect of different bisnaphtalimidopropil derivatives on parasite growth. The results are representative of 5 assays made independently. The promastigote and axenic amastigote were incubated with a serial range of drug concentrations 0.30 to 12.5 µM, at 27° C. and 3.125 to 100 µM at 37° C. in 5% $CO_2$, respectively, during 3 days. The growth curves represented indicate the percentage growth related to the control for each concentration after luciferase activity determination. Each point represents a mean of 3 assays±STD.

The treatment of different forms of the parasite *Leismania infantum*, promastigote, axenic amastigote and intracellular amastigote, with the compounds, BNIPSpd, BNIPPut, BNIPDaoct, BNIPDanon, BNIPDpta, BNIPDeta, in range of concentration 0.39 to 12.50 µM resulted in a dose dependent inhibition of parasite growth, except to the axenic amastigote incubated with BNIPDaoct, which didn't inhibited the parasite growth up to 50 µM concentration (FIG. 1). We have observed that the parasite growth was completely blocked after 6.25 µM to the promastigote and 50 µM to the axenic amastigote, except to the BNIPDaoct.

In the case of promastigote, the $IC_{50}$±SD determined were 1.86±0.82, 0.40±0.15, ≦0.39, 2.09±0.54, 1.09±0.12, 0.96±0.17, for BNIPSpd, BNIPPut, BNIPDaoct, BNIPDanon, BNIPDpta, BNIPDeta, respectively. The most active compound for this parasite form was BNIPDoct.

In case of axenic amastigote form the $IC_{50}$±SD determined were 9.61±1.84, 5.49±0.67, ≧50.00, 17.42±0.97, 5.24±0.93, 6.97±0.20 µM, for the following compounds BNIPSpd, BNIPPut, BNIPDaoct, BNIPDanon, BNIPDpta, BNIPDeta, respectively. The most active compound for this parasitic form was BNIPDpta.

In the case of intracellular amastigote form the $IC_{50}$±SD determined were 8.92±1.07, 4.53±0.54, 2.43±0.19, 6.03±0.67, 4.22±1.07, 9.52±0.56 µM, for the following compounds, BNIPSpd, BNIPPut, BNIPDaoct, BNIPDanon, BNIPDpta, BNIPDeta, respectively. The most active compound for this parasitic form was BNIPDaoct. According to the results obtained all the compounds in study have antiparasitic activity that give potential drugs to the leishmaniase treatment.

TABLE 2

Cytotoxicity of bisnaphthalimidopropil derivative compounds in different forms of the parasite *Leishmania infantum*

| | $IC_{50}$(µM) | | |
|---|---|---|---|
| Compounds | Promastigotes | Amastigotes axenic | Amastigote intracellular |
| BNIPSpd | 1.86 ± 0.82 | 9.61 ± 1.84 | 8.92 ± 1.07 |
| BNIPPut | 0.40 ± 0.15 | 5.49 ± 0.67 | 4.53 ± 0.54 |
| BNIPDapen | ND | ND | ND |
| BNIPDahex | ND | ND | ND |
| BNIPDahep | ND | ND | ND |
| BNIPDaoct | ≦0.39 | ≧50.00 | 2.43 ± 0.19 |
| BNIPDanon | 2.09 ± 0.54 | 17.42 ± 0.97 | 6.03 ± 0.67 |
| BNIPDadec | ND | ND | ND |

TABLE 2-continued

Cytotoxicity of bisnaphthalimidopropil derivative compounds in different forms of the parasite Leishmania infantum

| | | IC$_{50}$(μM) | |
|---|---|---|---|
| Compounds | Promastigotes | Amastigotes axenic | Amastigote intracellular |
| BNIPDadod | ND | ND | ND |
| BNIPDpta | 1.09 ± 0.12 | 5.24 ± 0.93 | 4.22 ± 1.07 |
| BNIPDeta | 0.96 ± 0.17 | 6.97 ± 0.20 | 9.52 ± 0.56 |

Cytotoxicity determined by luciferase assay. The results were obtained after treatment of different parasite forms with a range of different drug concentrations 0.30 to 100 μM after 72 h of incubation. The results were representative of medium±SD at least 5 assays. ND: not determined.

In conclusion, the new bisnaphthalimidopropyl derivatives exhibit cytotoxicity that may be further developed as anti-tumour and/or anti-parasitic therapeutic agents.

Conclusion

The use of the compounds in formula I, II, III, IV, V, VI, VII, VIII, IX, X, XI could be an advantage in the treatment of cancer and parasitic disease namely, treatment of leishmaniasis, trypanosomiasis and malaria.

For preparation of the pharmaceutical compositions with the compounds of formula I, II, III, IV, V, VI, VII, VIII, IX, X, XI, a inert pharmaceutical adjuvant are mixed with active compounds. The adjuvant used could be solid or liquid. The solid forms include powder, pill, grainy disperse and capsule. The solid adjuvant could be one or more substance that could be diluents, flavouring agents, sweeteners, solvents, lubricants, suspension agents, binding agents or disaggregating agents and could be a encapsulating agents.

The pharmaceutical preparation is preferentially presented on single dose form, the package contains discrete quantities of the preparation as cover pills, capsules, power in flask or ampoule and liposome formula.

The dose could range according to the needs of the animal or the patient, the severity of the disease and the compound to be used. The determinations of the dose for a particular situation regards to the people skilled in the art. For convenience, the total daily dose could be devised and distributed administration during the day.

DETAILED DESCRIPTION OF THE INVENTION

General Method for the Synthesis of Mesitylated Di or Triamine

Corresponding diamine or triamine was dissolved in anhydrous pyridine followed by the addition of mesitylene chloride (2.1 molar excess for diamine and 3.1 molar excess for triamine). The resulting solution was stirred at room temperature for 4 hours. Removal of the pyridine followed by the addition of cold water resulted in the formation of a precipitate. The latter was filtered off and washed thoroughly with water. The crude product was recrystallised from absolute ethanol.

$N^1,N^8$-Dimesityloctane 2-(70%), $^{13}$C NMR (CDCl$_3$) δ: 20.82 (CH$_3$, Mts), 22.85 (CH$_3$, Mts), 26.34 (CH$_2$), 28.70 (CH$_2$), 29.41 (CH$_2$), 41.05 (N—CH$_2$), 47.58 (CH$_2$), 133 (Aromatic carbons, Mts).

$N^1,N^9$-Dimesitylnonane 3-(36%), $^{13}$C NMR (CDCl$_3$) δ: 20.82 (CH$_3$, Mts), 22.85 (CH$_3$, Mts), 26.34 (CH$_2$), 28.70 (CH$_2$), 29.41 (CH$_2$), 41.05 (N—CH$_2$), 47.58 (CH$_2$), 133 (Aromatic carbons, Mts).

$N^1,N^{10}$-Dimesityldecane 4-(48%), $^{13}$C NMR (CDCl$_3$) δ: 20.82 (CH$_3$, Mts), 22.85 (CH$_3$, Mts), 26.34 (CH$_2$), 28.70 (CH$_2$), 29.41 (CH$_2$), 41.05 (N—CH$_2$), 47.58 (CH$_2$), 133 (Aromatic carbons, Mts).

$N^1,N^5,N^9$-Trimesityldipropyltriamine 5-(67%), $^{13}$C NMR (CDCl$_3$) δ: 20.85 (CH$_3$, Mts), 22.79 (CH$_3$, Mts), 27.69 (CH$_2$), 39.50 (N—CH$_2$), 43.11 (N—CH$_2$), 132.17 (Aromatic carbons, Mts), 139.98 (Aromatic carbons, Mts).

$N^1,N^3,N^6$-Trimesityldiethyltriamine 6-(59%), $^{13}$C NMR (CDCl$_3$) δ: 21.35 (CH$_3$, Mts), 23.06 (CH$_3$, Mts), 41.05 (N—CH$_2$), 47.58 (N—CH$_2$), 133 (Aromatic carbons, Mts).

Synthesis of O-tosylpropylnaphthalimide

Naphthalic anhydride (6.34 g, 0.032 mol) was dissolved in DMF (50 mL) followed by the addition of aminopropanol 3 (2.45 g, 0.032 mol) and DBU (4.87 g, 0.032 mol). The solution was left stirring at 85° C. for 4 hr. The solvent DMF was removed under reduced pressure and the resulting residue was poured into cold water with stirring (200 mL) to form a precipitate. The latter was filtered using a buchner funnel and washed thoroughly with (i) water (ii) saturated bicarbonate solution. The yield of the reaction was found to be 95%. This compound, Naphthalimidopropanol was pure enough and was used in the next step with no further purification. NMR (CDCl$_3$): δ=8.65-7.80 (m, 6H, aromatic protons), 4.39 (t, 2H, —N—CH$_2$), 3.69 (t, 2H, CH$_2$—O—), 3.20 (s, broad, 1H, OH), 2.06 (p, 2H, CH$_2$). $^{13}$C NMR (CDCl$_3$): δ=161.70 (C=O), 135.70-122.90 (aromatic carbons), 74.90, 59.90, 30.90 (3×CH$_2$).

Naphthalimidopropanol (5.10 g, 20 mmol) was dissolved in anhydrous pyridine (80 mL). The solution was stirred for 15 mins at 4° C. Tosyl Chloride (5.72 g, 30 mmol) were added, in small portions, over 30 mins. The solution was left overnight at 4° C. and was poured into ice water (200 mL) to form a solid on standing. The solid formed was filtered off and washed thoroughly with water. The crude product was recrystallised from either ethanol or ethylacetate to give O-tosylpropylnaphthalimide 6 (53%). $^1$H NMR (CDCl$_3$): δ=8.65-7.80 (m, 6H, aromatic protons), 4.45 (t, 2H, CH$_2$), 4.35 (t, 2H, CH$_2$), 2.50 (s, 3H, CH$_3$), 2.25 (p, 2H, CH$_2$). $^{13}$C NMR (CDCl$_3$): δ=161.30 (C=O), 145.10-123.10 (aromatic carbons), 73.10, 67.90, 28.70 (3×CH$_2$), 22.10 (CH$_3$). LRMS (FAB): Calcd. for C$_{12}$H$_{19}$NO$_6$S 425.09, Found: 426 [MH]$^+$.

General N-Alkylation Reaction (Step 1 in Scheme 1)

Mesitylated polyamines (2-6) (0.651 mmol) were dissolved in anhydrous DMF (13.5 mL) followed by the addition of 7 (0.13 mmol) and cesium carbonate (1.06 g). The solution was left at 85° C. and completion of the reaction was monitored by thin layer chromatography. DMF was removed under vacuo and the residue was poured into cold water and the resulted precipitate filtered and washed thoroughly with water. After drying the crude was recrystallised from ethanol to give the fully protected pure product in high yield (75-85%).

General Deprotection Reaction (Step 2 in Scheme 1)

The fully protected polyamine derivatives (0.222 mmol) were dissolved in anhydrous dichloromethane (10 mL) followed by the addition of hydrobromic acid/glacial acetic acid (1 mL). The solution was left stirring at room temperature for 24 h. The yellow precipitate formed, was filtered off and washed with dichloromethane, ethylacetate and ether.

Using the process described and related processes, currently used by the ones skilled in the art, using alkyl chain appropriated, were synthesized, Bisnaphthalimidopropyldiaminopentane (BNIPDapen). LRMS (ESI): calc C$_{35}$H$_{36}$N$_4$O$_4$2HBr 738.52 [M]$^+$, found: 657.1 [M-H-2Br]$^+$.

Bisnaphthalimidopropyldiaminohexane (BNIPDahex). LRMS (ESI): calc C$_{36}$H$_{38}$N$_4$O$_4$2HBr 752.71 [M]$^+$, found: 671.3 [M-H-2Br]$^+$.

Bisnaphthalimidopropyldiaminoheptane (BNIPDahep). RMS (ESI): calc $C_{37}H_{40}N_4O_4$2HBr 766.74 [M]$^+$, found: 671.3 [M-H-2Br]$^+$.

Bisnaphthalimidopropyldiaminooctane—(BNIPDaoct) (85%), DMSO-$d_6$, δ: 24.43 (CH$_2$), 25.30 (CH$_2$), 25.66 (CH$_2$), 28.07 (CH$_2$), 44.72 (N—CH$_2$), 46.60 (N—CH$_2$), 121.99, 127.13, 130.62, 131.21, 134.31 (Aromatic Carbons), 163.61 (C=O). LRMS (FAB): Calcd. for $C_{38}H_{42}N_4O_4$H 619.3279, Found: 619.3282 [M-H-2Br]$^+$.

Bisnaphthalimidopropyldiaminononane (BNIPDanon) (85%), DMSO-$d_6$, δ: 24.88 (CH$_2$), 25.84 (CH$_2$), 26.16 (CH$_2$), 28.76 (CH$_2$), 45.29 (N—CH$_2$), 47.29 (N—CH$_2$), 121.94, 127.51, 131.12, 131.42, 134.76 (Naphthalimido aromatic Carbons), 164.00 (C=O). LRMS (FAB): Calcd. for $C_{39}H_{44}N_4O_4$H 633.3435, Found: 633.3440 [M-H-2Br]$^+$.

Bisnaphthalimidopropyldiaminodecane (BNIPDadec) (75%), DMSO-$d_6$, δ: 24.97 (CH$_2$), 25.90 (CH$_2$), 26.22 (CH$_2$), 28.79 (CH$_2$), 29.00 (CH$_2$), 45.35 (N—CH$_2$), 47.38 (N—CH$_2$), 121.05, 127.66, 131.30, 131.51, 134.94 (Naphthalimido aromatic Carbons), 164.21 (C=O). LRMS (FAB): Calcd. for $C_{40}H_{46}N_4O_4$H 647.4, Found: 647.4 [M-H-2Br]$^+$.

Bisnaphthalimidopropyldiaminododecane (BNIPDadod). LRMS (FAB): Calcd. for $C_{42}H_{50}N_4O_4$H 836.71, Found: 675.4 [M-2H-2Br]$^+$.

Bisnaphthalimidopropyldipropiltriamine (BNIPDpta) (85%), DMSO-$d_6$, δ: 22.20 (CH$_2$), 24.70 (CH$_2$), 44.10 (N—CH$_2$), 44.20 (N—CH$_2$), 45.00 (N—CH$_2$), 130 (Aromatic Carbons) 164.87 (C=O). LRMS (FAB): Calcd. for $C_{36}H_{39}N_5O_4$3HBr 850.7, Found: 606.4 [M-2H-3Br]$^+$.

Bisnaphthalimidopropyldietiltriamine (BNIPDeta) (67%), DMSO-$d_6$, δ: 22.20 (CH$_2$), 24.70 (CH$_2$), 44.10 (N—CH$_2$), 44.20 (N—CH$_2$), 45.00 (N—CH$_2$), 130 (Aromatic Carbons). LRMS (FAB): Calcd. for $C_{34}H_{35}N_5O_4$3HBr 820.40, 578.2762 [M-2H-3Br]$^+$. Found: 578.2760 [M-2H-3Br]$^+$.

Example 1

Synthesis of BNIPDaoct

The diamine was dissolved in anhydrous pyridine followed by the addition of mesitylene chloride (2.1 molar excess). The resulting solution was stirred at room temperature for 4 hours. Removal of the pyridine followed by the addition of cold water resulted in the formation of a precipitate. The latter was filtered off and washed thoroughly with water. The crude product was recrystallised from absolute ethanol.

$N^1$,$N^8$-Dimesityloctane 2-(70%), $^{13}$C NMR (CDCl$_3$) δ: 20.82 (CH$_3$, Mts), 22.85 (CH$_3$, Mts), 26.34 (CH$_2$), 28.70 (CH$_2$), 29.41 (CH$_2$), 41.05 (N—CH$_2$), 47.58 (CH$_2$), 133 (Aromatic carbons, Mts).

The naphthalic anhydride (6.34 g, 0.032 mol) was dissolved in DMF (50 mL) followed by the addition of aminopropanol 3 (2.45 g, 0.032 mol) and DBU (4.87 g, 0.032 mol). The solution was left stirring at 85° C. for 4 hr. The solvent DMF was removed under reduced pressure and the resulting residue was poured into cold water with stirring (200 mL) to form a precipitate. The latter was filtered using a buchner funnel and washed thoroughly with (i) water (ii) saturated bicarbonate solution. The yield of the reaction was found to be 95%. This compound, Naphthalimidopropanol was pure enough and was used in the next step with no further purification. NMR (CDCl$_3$): δ=8.65-7.80 (m, 6H, aromatic protons), 4.39 (t, 2H, —N—CH$_2$), 3.69 (t, 2H, CH$_2$—O—), 3.20 (s, broad, 1H, OH), 2.06 (p, 2H, CH$_2$). $^{13}$C NMR (CDCl$_3$): δ=161.70 (C=O), 135.70-122.90 (aromatic carbons), 74.90, 59.90, 30.90 (3×CH$_2$).

Naphthalimidopropanol (5.10 g, 20 mmol) was dissolved in anhydrous pyridine (80 mL). The solution was stirred for 15 mins at 0° C. Tosyl Chloride (5.72 g, 30 mmol) were added, in small portions, over 30 mins. The solution was left overnight at 4° C. and was poured into ice water (200 mL) to form a solid on standing. The solid formed was filtered off and washed thoroughly with water. The crude product was recrystallised from either ethanol or ethylacetate to give O-tosylpropylnaphthalimide 6 (53%). $^1$H NMR (CDCl$_3$): δ=8.65-7.80 (m, 6H, aromatic protons), 4.45 (t, 2H, CH$_2$), 4.35 (t, 2H, CH$_2$), 2.50 (s, 3H, CH$_3$), 2.25 (p, 2H, CH$_2$). $^{13}$C NMR (CDCl$_3$): δ=161.30 (C=O), 145.10-123.10 (aromatic carbons), 73.10, 67.90, 28.70 (3×CH$_2$), 22.10 (CH$_3$). LRMS (FAB): Calcd. for $C_{12}H_{19}NO_6$S 425.09, Found: 426 [MH]$^+$.

The mesitylated polyamines (0.651 mmol) were dissolved in anhydrous DMF (13.5 mL) followed by the addition of 7x (0.13 mmol) and cesium carbonate (1.06 g). The solution was left at 85° C. and completion of the reaction was monitored by thin layer chromatography. DMF was removed under vacuo and the residue was poured into cold water and the resulted precipitate filtered and washed thoroughly with water. After drying the crude was recrystallised from ethanol to give the fully protected pure product in high yield (75-85%).

The fully protected polyamine derivatives (0.222 mmol) were dissolved in anhydrous dichloromethane (10 mL) followed by the addition of hydrobromic acid/glacial acetic acid (1 mL). The solution was left stirring at room temperature for 24 h. The yellow precicipate formed, was filtered off and washed with dichloromethane, ethylacetate and ether.

By this way were synthesized the Bisnaphthalimidopropyl-diaminooctane (BNIPDaoct) (85%), DMSO-$d_6$, δ: 24.43 (CH$_2$), 25.30 (CH$_2$), 25.66 (CH$_2$), 28.07 (CH$_2$), 44.72 (N—CH$_2$), 46.60 (N—CH$_2$), 121.99, 127.13, 130.62, 131.21, 134.31 (Aromatic Carbons), 163.61 (C=O). LRMS (FAB): Calcd. for $C_{38}H_{42}N_4O_4$H 619.3279, Found: 619.3282 [M-H-2Br]$^+$.

Example 2

Synthesis of BNIPDpta

The dipropiltriamine was dissolved in anhydrous pyridine followed by the addition of mesitylene chloride (3.1 molar excess). The resulting solution was stirred at room temperature for 4 hours. Removal of the pyridine followed by the addition of cold water resulted in the formation of a precipitate. The latter was filtered off and washed thoroughly with water. The crude product was recrystallised from absolute ethanol. $N^1$,$N^5$,$N^9$-Trimesityldipropyltriamine 5-(67%), $^{13}$C NMR (CDCl$_3$) δ: 20.85 (CH$_3$, Mts), 22.79 (CH$_3$, Mts), 27.69 (CH$_2$), 39.50 (N—CH$_2$), 43.11 (N—CH$_2$), 132.17 (Aromatic carbons, Mts), 139.98 (Aromatic carbons, Mts).

The naphthalic anhydride (6.34 g, 0.032 mol) was dissolved in DMF (50 mL) followed by the addition of aminopropanol 3 (2.45 g, 0.032 mol) and DBU (4.87 g, 0.032 mol). The solution was left stirring at 85° C. for 4 hr. The solvent DMF was removed under reduced pressure and the resulting residue was poured into cold water with stirring (200 mL) to form a precipitate. The latter was filtered using a buchner funnel and washed thoroughly with (i) water (ii) saturated bicarbonate solution. The yield of the reaction was found to be 95%. This compound, Naphthalimidopropanol was pure enough and was used in the next step with no further purification. NMR (CDCl$_3$): δ=8.65-7.80 (m, 6H, aromatic protons), 4.39 (t, 2H, —N—CH$_2$), 3.69 (t, 2H, CH$_2$—O—), 3.20 (s, broad, 1H, OH), 2.06 (p, 2H, CH$_2$). $^{13}$C NMR (CDCl$_3$): δ=161.70 (C═O), 135.70-122.90 (aromatic carbons), 74.90, 59.90, 30.90 (3×CH$_2$).

Naphthalimidopropanol (5.10 g, 20 mmol) was dissolved in anhydrous pyridine (80 mL). The solution was stirred for 15 mins at 4° C. Tosyl Chloride (5.72 g, 30 mmol) were added, in small portions, over 30 mins. The solution was left overnight at 4° C. and was poured into ice water (200 mL) to form a solid on standing. The solid formed was filtered off and washed thoroughly with water. The crude product was recrystallised from either ethanol or ethylacetate to give O-tosylpropylnaphthalimide 6 (53%). $^1$H NMR (CDCl$_3$): δ=8.65-7.80 (m, 6H, aromatic protons), 4.45 (t, 2H, CH$_2$), 4.35 (t, 2H, CH$_2$), 2.50 (s, 3H, CH$_3$), 2.25 (p, 2H, CH$_2$). $^{13}$C NMR (CDCl$_3$): δ=161.30 (C═O), 145.10-123.10 (aromatic carbons), 73.10, 67.90, 28.70 (3×CH$_2$), 22.10 (CH$_3$). LRMS (FAB): Calcd. for C$_{12}$H$_{19}$NO$_6$S 425.09, Found: 426 [MH]$^+$.

The mesitylated polyamines (0.651 mmol) were dissolved in anhydrous DMF (13.5 mL) followed by the addition of 7x (0.13 mmol) and cesium carbonate (1.06 g). The solution was left at 85° C. and completion of the reaction was monitored by thin layer chromatography. DMF was removed under vacuo and the residue was poured into cold water and the resulted precipitate filtered and washed thoroughly with water. After drying the crude was recrystallised from ethanol to give the fully protected pure product in high yield (75-85%).

The fully protected polyamine derivatives (0.222 mmol) were dissolved in anhydrous dichloromethane (10 mL) followed by the addition of hydrobromic acid/glacial acetic acid (1 mL). The solution was left stirring at room temperature for 24 h. The yellow precipitate formed, was filtered off and washed with dichloromethane, ethylacetate and ether.

By this way were synthesized the Bisnaphthalimidopropyl-dipropiltriamine (BNIPDpta) (85%), DMSO-d$_6$, δ: 22.20 (CH$_2$), 24.70 (CH$_2$), 44.10 (N—CH$_2$), 44.20 (N—CH$_2$), 45.00 (N—CH$_2$), 130 (Aromatic Carbons) 164.87 (C═O). LRMS (FAB): Calcd. for C$_{36}$H$_{39}$N$_5$O$_4$3HBr 850.7, Found: 606.4 [M-2H-3Br]$^+$.

BIBLIOGRAPHY

1. Brana, M. F.; Ramos, A. *Curr. Med. Chem. Anti-Cancer Agents.* 2001, 1, 237.
2. Kong Thoo Lin, P.; Pavlov, V. A. *Bioorganic and Medicinal Chemistry Letters,* 2000, 10, 1609.
3. Pavlov, V. A.; Kong Thoo Lin, P.; Rodilla, V. *Chemico-Biological Interactions,* 2001, 137, 15.
4. Patten, A. D.; Sun, J-H; Ardecky, R. J. U.S. Pat. No. 5,086,059, 1992.
5. Brana, M. F.; Castellano, J. M.; Moran, M.; Perez de Vega, M. J.; Qian, X. D.; Romerdahl, C. A.; Keilhauer, G. *European Journal of Medicinal Chemistry,* 1995, 30, 235.
6. Bailly, C.; Carrasco, C.; Joubert, A.; Bal, C.; Wattez, N.; Hildebrand, M-P.; Lansiaux, A.; Colson, P.; Houssier, C.; Cacho, M.; Ramos, A.; Brana, M. F. *Biochemistry,* 2003, 42, 4136.
7. Carrasco, C.; Joubert, A.; Tardy, C.; Maestre, N.; Cacho, M.; Brana, M. F.; Bailly, C. *Biochemistry,* 2003, 42, 11751.
8. Kong Thoo Lin, P.; Dance, A. M.; Bestwick, C.; Milne, L. *Biochemical Society Transactions,* 2003, 31, 407.
9. Pavlov, V. A.; Rodilla, V.; Kong Thoo Lin, P. *Life Sciences,* 2002, 71, 1161.
10. Dance, A. M.; Ralton, L.; Fuller, Z.; Milne, L.; Duthie, S.; Bestwick, C. S.; Kong Thoo Lin, P. *Biochemical Pharmacology,* 2005, 69, 19.
11. Tavares, J.; Quaissi, A.; Kong Thoo Lin, P.; Tomas, A.; Cordeiro-da-Silva, A. *International Journal for Parasitology,* 2005, 35, 637.
12. Murry, H. W. *Antimicrobial Agents and Chemotherapy,* 2001, 45, 2185.
13. Muller, S.; Coombs, G. H.; Walter, R. D. *Trends Parasitology,* 2001, 17, 242.
14. Fairlamb, A. H.; Cerami, A. *Annual Review Microbiology,* 1992, 46, 695.
15. Barrett, M. P.; Mottram, J. C.; Coombs, G. H. *Trends in Microbiology* 1999, 7, 82.
16. Thoo Lin, P. K. and. Pavlov, V. A. *Bioorganic and Medicinal Chemistry Letters,* 1998, 10, 1609.
17. Roy, G.; Dumas, C.; Sereno, D.; Wu, Y.; Singh, A. K.; Tremblay, M. J.; Ouellette, M.; Olivier, M.; and Papadopoulou, B. *Molecular and Biochemical Parasitology,* 2000, 110, 195.

The invention claimed is:
1. A compound selected from
(i) Bisnaphthalimidopropyldiaminooctane of structural formula:

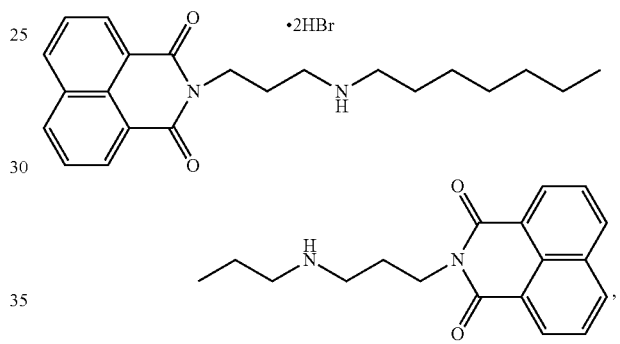

(ii) Bisnaphthalimidopropyldiaminononane of structural formula:

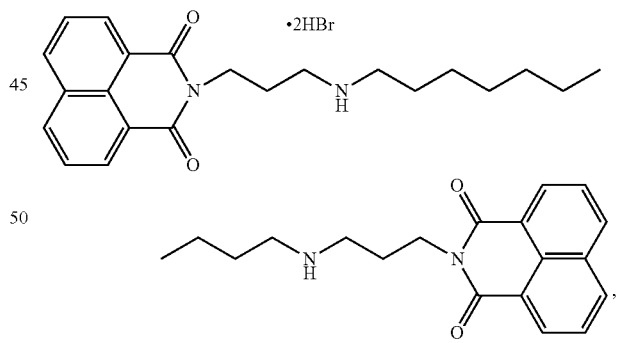

(iii) Bisnaphthalimidopropyldiaminodecane of structural formula:

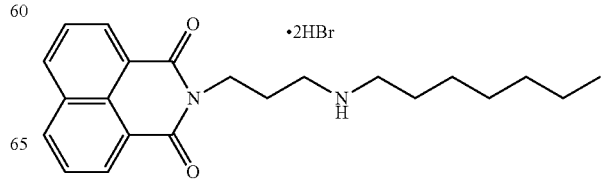

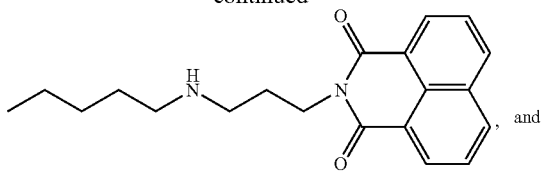, and (iv) Bisnaphthalimidopropyldiaminododecane of structural formula:

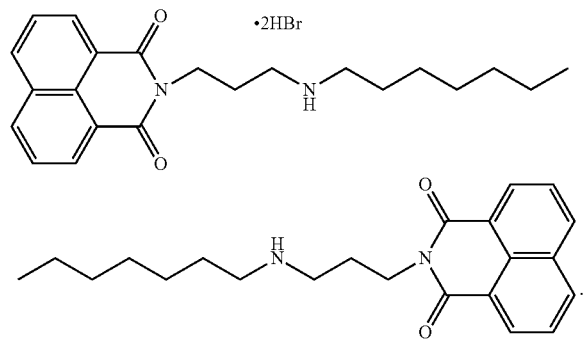

2. A pharmaceutical composition comprising as an active ingredient at least one compound according to claim 1, in association with a pharmaceutically acceptable vehicle or excipient.

3. The pharmaceutical composition of claim 2, further comprising at least one compound selected from the group consisting of miltefosine, amphotericin B, pentamidine, melarsoprol, benzimidazol, nifurtimox, ketoconazol, difluoromethylornitine, chloroquine, and quinine.

4. A method of treating parasitic diseases, comprising administering to a patient in need thereof, an affective amount of at least one compound of claim 1.

5. The method of treating parasitic diseases according to claim 4, wherein the parasitic disease is selected from the group consisting of trypanosomiasis, leishmaniasis and malaria.

6. A method of treating infectious conditions induced by a genus of parasites selected from the group consisting of *Leishmania, Trypanosoma,* and *Pasmodium,* comprising administering to a patient in need thereof an effective amount of at least one compound according to claim 1.

7. The method of treating infectious conditions according to claim 6, wherein the infectious condition is induced by a species selected from the group consisting of *L. infantum, L. donovani, L. major, L. tropica, L. mexicana, L. amazonensis, L. braziliensis, T. cruzi, T. brucei, T. gambiense, P. falciparum, P. vivax,* and *P. ovale*.

8. A method of treating cancer, comprising administering to a patient in need thereof, an effective amount of at least one of the compounds of claim 1.

* * * * *